(12) United States Patent
Hirono

(10) Patent No.: US 11,147,432 B2
(45) Date of Patent: Oct. 19, 2021

(54) ENDOSCOPE

(71) Applicant: OLYMPUS CORPORATION, Tokyo (JP)

(72) Inventor: Takayoshi Hirono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 331 days.

(21) Appl. No.: 16/243,185

(22) Filed: Jan. 9, 2019

(65) Prior Publication Data
US 2019/0142245 A1 May 16, 2019

Related U.S. Application Data

(63) Continuation of application No. PCT/JP2017/008944, filed on Mar. 7, 2017.

(30) Foreign Application Priority Data

Sep. 1, 2016 (JP) .............................. JP2016-170785

(51) Int. Cl.
*A61B 1/00* (2006.01)
*A61B 1/005* (2006.01)
(Continued)

(52) U.S. Cl.
CPC ........ *A61B 1/00068* (2013.01); *A61B 1/0052* (2013.01); *A61B 1/0057* (2013.01);
(Continued)

(58) Field of Classification Search
CPC ............ A61B 1/00068; A61B 1/00114; A61B 1/00117; A61B 1/00121; A61B 1/0052;
(Continued)

(56) References Cited

U.S. PATENT DOCUMENTS 4,281,646 A * 8/1981 Kinoshita .......... A61B 1/00068
134/104.1
4,576,650 A * 3/1986 Yabe ...................... A61B 1/125
134/22.12
(Continued)

FOREIGN PATENT DOCUMENTS

EP 2656779 A1 10/2013
JP 2000126111 A 5/2000
(Continued)

OTHER PUBLICATIONS

International Search Report dated May 30, 2017 issued in PCT/JP2017/008944.

*Primary Examiner* — Aaron B Fairchild
(74) *Attorney, Agent, or Firm* — Scully, Scott, Murphy & Presser, P.C.

(57) ABSTRACT

An endoscope includes an insertion section configured to be inserted into a subject, an operation section configured to be consecutively provided on a proximal end side of the insertion section, a rigid partition wall provided inside the insertion section or inside the operation section and configured to maintain watertightness between a first space including an inside of the insertion section and a second space formed on a distal end side of the first space, and a first check valve provided in the partition wall and configured to block circulation of gas from the second space to the first space and circulate gas from the first space to the second space.

10 Claims, 8 Drawing Sheets

(51) Int. Cl.
   *A61B 1/015* (2006.01)
   *G02B 23/24* (2006.01)
   *A61B 1/12* (2006.01)
(52) U.S. Cl.
   CPC ...... *A61B 1/00114* (2013.01); *A61B 1/00117* (2013.01); *A61B 1/00121* (2013.01); *A61B 1/015* (2013.01); *G02B 23/24* (2013.01); *A61B 1/121* (2013.01)
(58) Field of Classification Search
   CPC ....... A61B 1/0057; A61B 1/015; A61B 1/012; A61B 1/121; A61B 1/126
   See application file for complete search history.

(56) References Cited

U.S. PATENT DOCUMENTS

| | | | |
|---|---|---|---|
| 5,419,311 A * | 5/1995 | Yabe | A61B 1/00091 600/124 |
| 6,547,721 B1 * | 4/2003 | Higuma | A61B 1/051 600/133 |
| 6,547,722 B1 | 4/2003 | Higuma et al. | |
| 2008/0183037 A1 * | 7/2008 | Ichikawa | A61B 1/0008 600/104 |
| 2012/0029287 A1 * | 2/2012 | Wieters | H01B 17/305 600/133 |
| 2012/0088975 A1 * | 4/2012 | Morimoto | A61B 1/015 600/159 |
| 2012/0316395 A1 * | 12/2012 | Koga | A61B 1/00101 600/157 |
| 2013/0197309 A1 | 8/2013 | Sakata | |
| 2014/0288372 A1 * | 9/2014 | Ando | A61B 1/00068 600/159 |

FOREIGN PATENT DOCUMENTS

| | | |
|---|---|---|
| JP | 2000157484 A | 6/2000 |
| JP | 2001025457 A | 1/2001 |
| JP | 2009056256 A | 3/2009 |
| JP | 5231691 B1 | 7/2013 |
| WO | 2013114703 A1 | 8/2013 |

* cited by examiner

ENDOSCOPE

CROSS REFERENCE TO RELATED APPLICATION

This application is a continuation application of PCT/JP2017/008944 filed on Mar. 7, 2017 and claims benefit of Japanese Application No. 2016-170785 filed in Japan on Sep. 1, 2016, the entire contents of which are incorporated herein by this reference.

BACKGROUND OF THE INVENTION

1. Field of the Invention

The present invention relates to an endoscope having a more reliable waterproof structure by reducing entrance of vapor into a distal end portion at a time of autoclave sterilization treatment.

2. Description of the Related Art

Conventionally, an endoscope configured by including an insertion section having an elongated tubular shape has been widely used in a medical field and an industrial field, for example. A medical endoscope used in the medical field is configured to allow an insertion section to be inserted into a subject, e.g., a body cavity of a living body to observe an organ or the like and subject the organ or the like to various types of treatments using a treatment instrument inserted into a treatment instrument insertion channel provided in the endoscope, as needed. An industrial endoscope used in the industrial field is configured to allow an insertion section to be inserted into an object, e.g., an apparatus or mechanical equipment such as a jet engine or a factory piping and observe and inspect a state inside the object, e.g., a state of damage or corrosion.

The endoscope used in the medical field among the conventional endoscopes of the type is usually configured to have a watertight structure to enable immersion in a medicinal solution, for example.

On the other hand, the endoscope used in the medical field, for example, among the conventional endoscopes of the type has been required, after being used in endoscope inspection, to allow cleaning to be reliably performed and at the same time allow disinfection and sterilization treatment for another use in another inspection or the like to be reliably performed. In this case, as a method for cleaning and disinfection or sterilization treatment in the endoscope in the medical field, autoclave sterilization treatment, for example, has been widely performed in recent years.

Generally, when autoclave sterilization treatment is performed, a process for introducing an endoscope having a watertight structure into a sterilization chamber and depressurizing an inside of the sterilization chamber is performed. At the time of the depressurization process, gas inside the endoscope introduced into the sterilization chamber may expand. Due to this, since a distal end portion and a bending portion, for example, of the endoscope are covered with a flexible outer cover tube, when internal gas expands, the outer cover tube may also expand, deform, or burst.

Therefore, a conventional endoscope is configured by providing a partition member configured to seal a first internal space covered with a flexible outer cover tube inside a distal end portion and a bending portion of the endoscope and a second internal space including a flexible tube and an operation section in a watertight manner while providing a light guide connector provided at a distal end of a universal cable extending from the operation section with an air vent port causing an inside and an outside of the endoscope to communicate with each other, as disclosed in Japanese Patent Application Laid-Open Publication No. 2000-126111, for example. When inspection is performed using the endoscope, a cap is mounted on the air vent port to close the air vent port in a watertight manner. On the other hand, when the endoscope is subjected to autoclave sterilization treatment, the cap is removed to open the air vent port when the endoscope is introduced into a sterilization chamber. By such a configuration, even if vapor at the time of autoclave sterilization treatment enters the endoscope via the air vent port, the vapor remains in the second internal space by the partition member and does not reach an inside of the first internal space in the endoscope described in Japanese Patent Application Laid-Open Publication No. 2000-126111. Thus, internal constituent members (an electric component, a metal component, etc., in particular) in the first internal space are not exposed to vapor. Accordingly, the constituent members can be prevented from deteriorating due to vapor in autoclave sterilization treatment.

In a configuration described in Japanese Patent Application Laid-Open Publication No. 2000-126111, described above, a capacity of the second internal space is made larger than a capacity of the first internal space while the first internal space is filled with a flowable filler. The configuration produces an effect of being able to prevent the outer cover tube from deforming and bursting due to gas within the first internal space expanding at the time of autoclave sterilization treatment because presence of the gas within the first internal space is reduced.

As disclosed in Japanese Patent Application Laid-Open Publication No. 2000-157484, for example, in addition to a configuration in which a light guide connector is provided with an air vent port, like in Japanese Patent Application Laid-Open Publication No. 2000-126111, a configuration in which a check valve capable of opening and closing the air vent port, as needed, is further provided. The check valve has a function of bringing the air vent port into an open state when air pressure inside the endoscope becomes higher than air pressure outside the endoscope while maintaining a closed state of the air vent port when the air pressure inside the endoscope is lower than the air pressure outside the endoscope.

According to the configuration, the air pressure inside the endoscope becomes higher than the air pressure outside the endoscope at the time of a depressurization process when autoclave sterilization treatment is performed. Thus, the check valve brings the air vent port into the open state. As a result, a difference between the respective pressures inside and outside the endoscope can be eliminated. Accordingly, the configuration produces an effect of being able to prevent gas inside the endoscope from expanding at the time of the depressurization process and prevent the outer cover tube covering the bending portion from deforming and bursting, for example.

SUMMARY OF THE INVENTION

To achieve the above described object, an endoscope according to an aspect of the present invention includes an insertion section configured to be inserted into a subject, an operation section configured to be consecutively provided on a proximal end side of the insertion section, a rigid partition wall provided inside the insertion section or inside the operation section and configured to maintain watertightness between a first space including an inside of the insertion section and a second space formed on a distal end side of the first space, and a first check valve provided in the partition wall and configured to block circulation of gas from the second space to the first space and circulate gas from the first space to the second space.

DETAILED DESCRIPTION OF THE PREFERRED EMBODIMENTS

Figure 1:
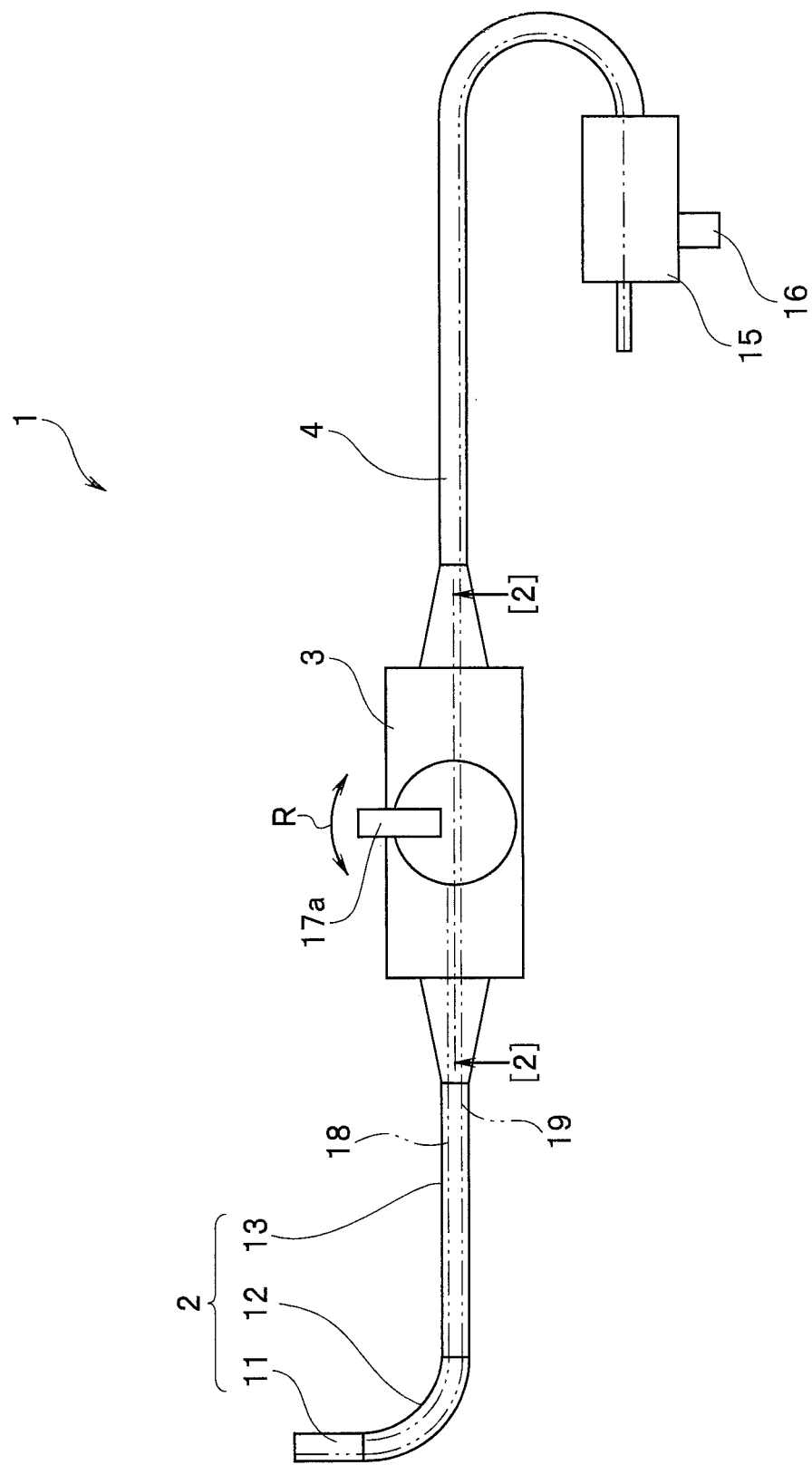
FIG. 1 is a diagram illustrating a schematic configuration of an endoscope according to a first embodiment of the present invention.

The present invention will be described below using illustrated embodiments. Each of drawings used in the following description is schematic, and a dimensional relationship among members and a scale of each of the members, for example, may be made different for each of components to illustrate the respective components in a size which is recognizable on the drawing. Therefore, the present invention is not limited to only an illustrated form for a quantity of the respective components described in each of the drawings, a shape of each of the components, a ratio of respective sizes of the components, and a relative positional relationship among the respective components, for example.

First Embodiment

Figure 2:
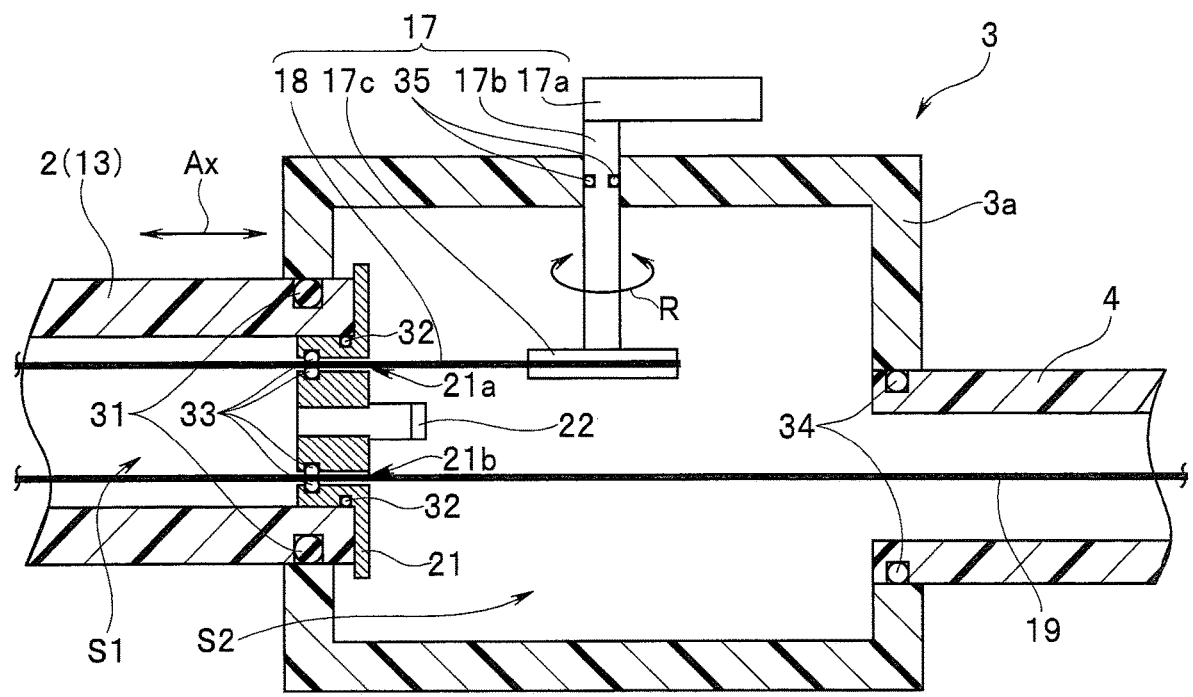
FIG. 2 is a diagram illustrating an outline of an internal configuration of a connection site among an insertion section, an operation section, and a universal cable in the endoscope illustrated in FIG. 1 (a cross-sectional view along a line [2]-[2] in FIG. 1)
Figure 3:
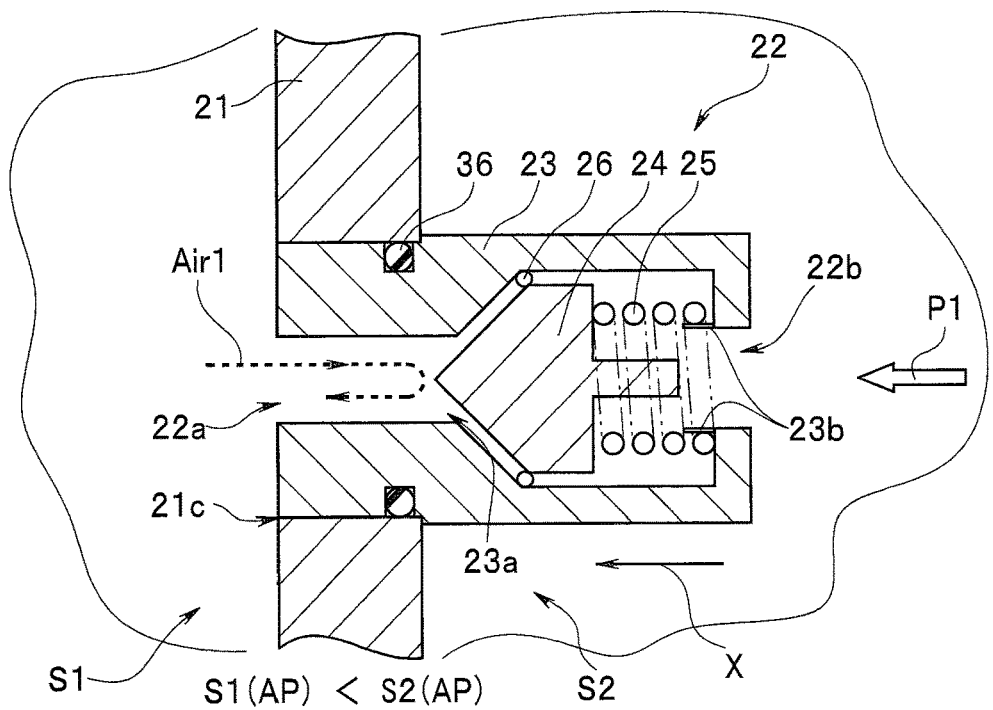
FIG. 3 is a diagram illustrating a schematic configuration of a first check valve provided in the endoscope illustrated in FIG. 1 and illustrating a closed state of the first check valve.
Figure 4:
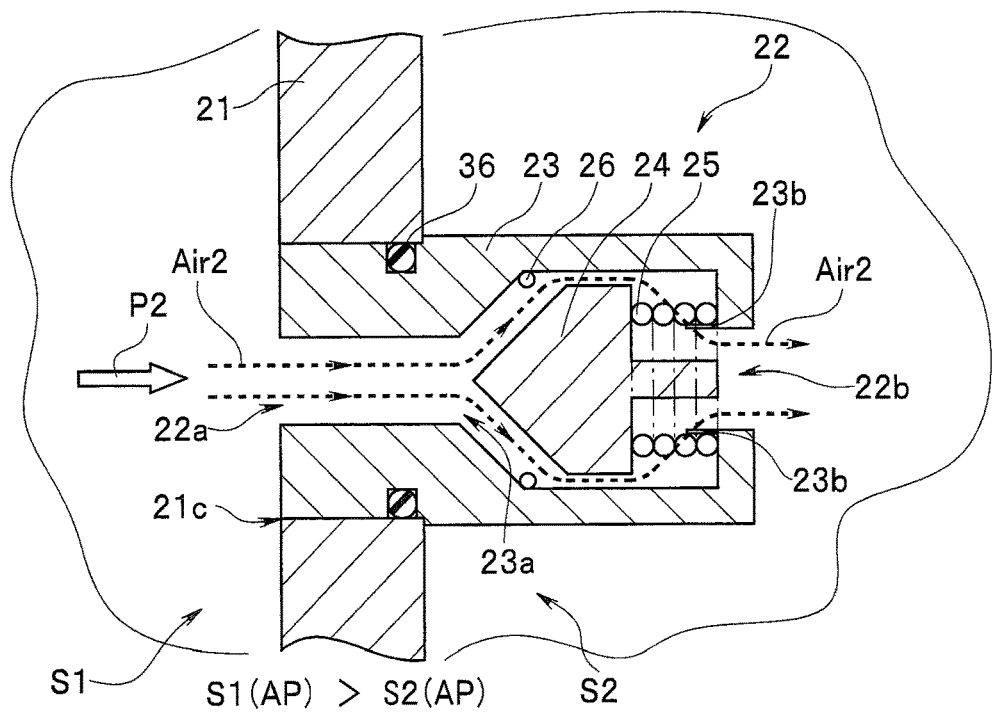
FIG. 4 is a diagram illustrating a schematic configuration of the first check valve provided in the endoscope illustrated in FIG. 1 and illustrating an open state of the first check valve.
Figure 5:
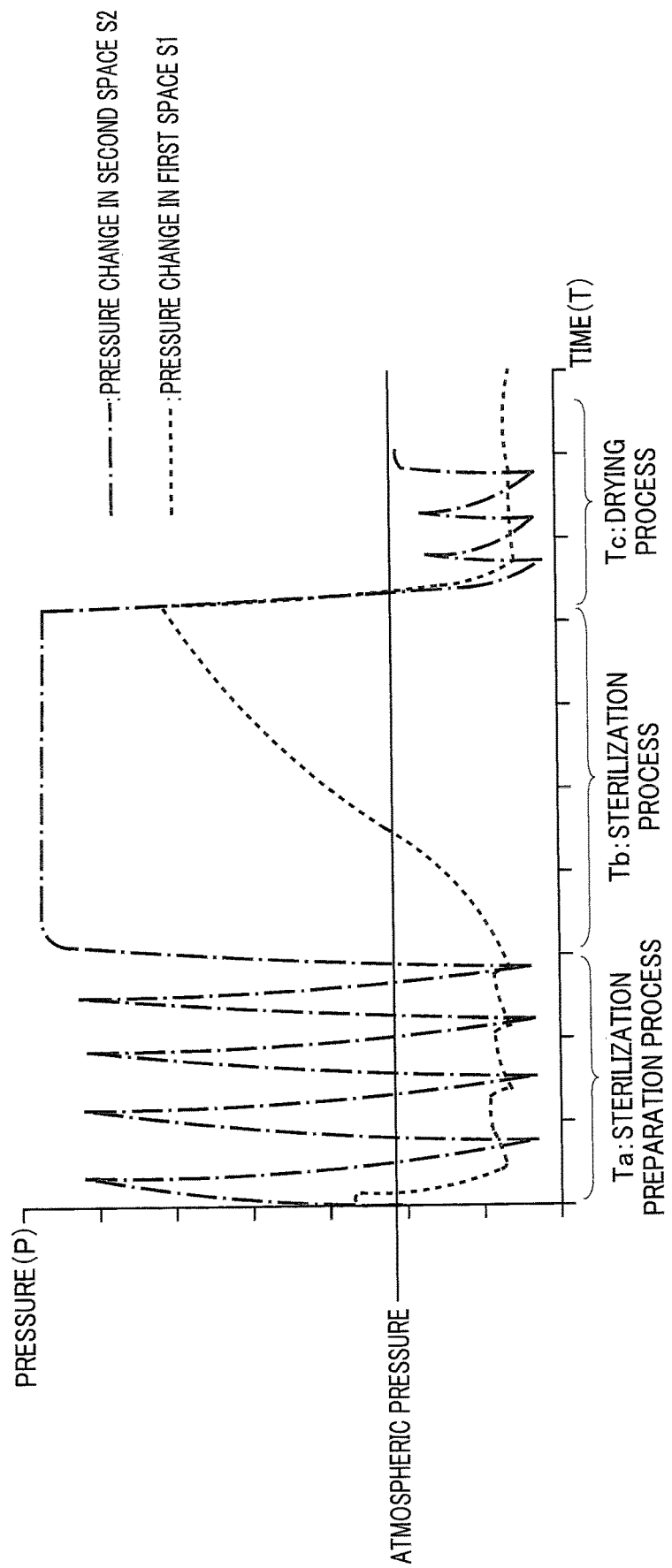
FIG. 5 is a graph illustrating respective air pressure changes in an internal space (a first space and a second space) of the endoscope illustrated in FIG. 1 when the endoscope is subjected to autoclave sterilization treatment.

FIGS. 1 to 5 are diagrams describing a first embodiment of the present invention, where FIG. 1 is a diagram illustrating a schematic configuration of an endoscope according to the first embodiment of the present invention, and FIG. 2 is a diagram illustrating an outline of an internal configuration of a connection site among an insertion section, an operation section, and a universal cable in the endoscope illustrated in FIG. 1. Note that FIG. 2 illustrates a cross section along a line [2]-[2] illustrated in FIG. 1. FIGS. 3 and 4 are diagrams each illustrating a schematic configuration of a first check valve provided in the endoscope illustrated in FIG. 1. FIG. 3 illustrates a closed state of the first check valve. FIG. 4 illustrates an open state of the first check valve. FIG. 5 is a graph illustrating air pressure changes in an internal space (a first space and a second space) of the endoscope illustrated in FIG. 1 when the endoscope is subjected to autoclave sterilization treatment.

First, the schematic configuration of the endoscope according to the present embodiment will be described below with reference to FIGS. 1 to 4. As illustrated in FIG. 1, the endoscope 1 according to the present embodiment mainly includes an insertion section 2, an operation section 3, and a universal cable 4, for example, in the order from a distal end side to a proximal end side.

The insertion section 2 is a constituent section configured to be inserted into a body cavity of a subject when used as the endoscope 1. The insertion section 2 is formed in an elongated tubular shape having flexibility as a whole. The insertion section 2 is configured in a form of a distal end portion 11, a bending portion 12, and a flexible tube portion 13 consecutively provided in the order from the distal end side. Longitudinal members, e.g., a bending wire 18, an electrical signal line, and a light guide cable 19 are inserted into and arranged in the insertion section 2. Note that the bending wire 18 among the longitudinal members is inserted into the insertion section 2, and is disposed from the bending portion 12 in the insertion section 2 to a bending operation mechanism 17 (not illustrated in FIG. 1; see FIG. 2) inside the operation section 3. The electrical signal line and the light guide cable 19, for example, among the longitudinal members are inserted into the insertion section 2 and the operation section 3 from the distal end portion 11 in the insertion section 2, and are further inserted into the universal cable 4.

The operation section 3 is consecutively provided on a proximal end side of the insertion section 2. The operation section 3 includes a housing 3a (see FIG. 2), a plurality of operation members (e.g., an operation lever 17a) disposed on an outer surface of the housing 3a, and various types of constituent members accommodated and arranged inside the housing 3a, for example.

As illustrated in FIG. 2, the housing 3a is a rigid housing member formed in a box shape having an internal space. A proximal end of the flexible tube portion 13 in the insertion section 2 is consecutively provided on one surface of the housing 3a via a seal member 31 such as an O-shaped ring in a watertight manner. A proximal end of the universal cable 4 is consecutively provided on the other surface of the housing 3a via a seal member 34 such as an O-shaped ring in a watertight manner.

The longitudinal members from the insertion section 2 are provided to extend inside the housing 3a. The bending wire 18 among the longitudinal members connects to the bending operation mechanism 17 provided inside the operation section 3. The electrical signal line and the light guide cable 19, for example, among the longitudinal members are inserted into the operation section 3, and is further provided to extend into the universal cable 4.

The various types of constituent members are accommodated and arranged, as illustrated in FIG. 2, inside the housing 3a. The bending operation mechanism 17 including the operation lever 17a and configured to perform a bending operation of the bending portion 12 upon being operated by the operation lever 17a, a partition wall 21, and a first check valve 22, for example, are disposed inside the housing 3a.

The bending operation mechanism 17 includes the operation lever 17a, and mainly includes a rotating shaft 17b as an operation shaft and a pulley 17c, for example, in addition to the operation lever 17a, as shown in FIG. 2. Note that a configuration of the bending operation mechanism 17 is schematically illustrated for conceptual representation in FIG. 2. A basic configuration of the bending operation mechanism 17 is substantially similar to a basic configuration of a bending operation mechanism in an endoscope which has conventionally been generally put into practical use.

The operation lever 17a and the pulley 17c are respectively fixedly provided at one end and the other end of the rotating shaft 17b. The rotating shaft 17b is a rotation center of the operation lever 17a, and is an operation shaft member that operates to rotate when the operation lever 17a is operated.

The operation lever 17a is an operation member configured to input a rotation operation in a direction along an arrow R illustrated in FIGS. 1 and 2 with respect to the rotating shaft 17b.

The rotating shaft 17b is disposed to penetrate the one surface of the housing 3a in the operation section 3, and the rotating shaft 17b is rotatably pivoted to (a fixing portion of) the housing 3a. Between the rotating shaft 17b and the housing 3a, a seal member 35 such as an O-shaped ring configured to ensure watertightness between the rotating shaft 17b and the housing 3a is provided while permitting rotation of the rotating shaft 17b.

The pulley 17c is a constituent member configured to convert a rotation input from the operation lever 17a into an advance/retreat output toward an insertion axis of a bending wire 18. Therefore, the pulley 17c is formed in a substantially disk shape, and a groove portion around which the bending wire 18 is to be wound is formed on an outer peripheral surface of the pulley 17c. That is, one end of the bending wire 18 is fixed to the groove portion of the pulley 17c. When the pulley 17c rotates, the bending wire 18 is wound around the groove portion of the pulley 17c.

The bending operation mechanism 17 thus configured functions as follows. That is, a user performs an operation for rotating the operation lever 17a in a direction indicated by the arrow R. Consequently, the rotating shaft 17b and the pulley 17c rotate in the same direction. Consequently, the bending wire 18 advances or retreats in a direction of a long axis (a direction indicated by an arrow Ax in FIG. 2) along an insertion axis of the insertion section 2 while being wound around the groove portion of the pulley 17c. As a result, the bending portion 12 is bent in a predetermined direction.

The partition wall 21 is a wall member provided between a first space S1 and a second space S2 in the internal space of the endoscope 1 and separating both the spaces while maintaining watertightness between both the spaces. Note that the internal space of the endoscope 1 according to the present embodiment means a space where an internal space of the insertion section 2, an internal space of the operation section 3, and an internal space of the universal cable 4 communicate with one another. The internal space is partitioned to form two spaces, i.e., the first space S1 and the second space S2 by the partition wall 21 (see FIG. 2).

In the present embodiment, the first space S1 means the space including the internal space of the insertion section 2 out of the two spaces separated by the partition wall 21 in the internal space of the endoscope 1.

In the present embodiment, the second space S2 means the space other than the first space S1 out of the two spaces separated by the partition wall 21 in the internal space of the endoscope 1. That is, the second space S2 is a space formed at a position adjacent to a proximal end side of the first space S1 with the partition wall 21 sandwiched between the second space S2 and the first space S1. More specifically, the second space S2 corresponds to a space including the internal space of the operation section 3 and the internal space of the universal cable 4 (and the light guide connector 15) consecutively provided from the internal space of the operation section 3.

The partition wall 21 is configured using a rigid material, e.g., a metal member such as a stainless material. In the present embodiment, the partition wall 21 is provided to cover an opening portion on the proximal end side of the insertion section 2, as illustrated in FIG. 2, and a part of the partition wall 21 is disposed in a part of the internal space of the operation section 3.

The partition wall 21 is attached to an opening at a proximal end of the insertion section 2 by joining means such as fitting or adhesion in a watertight manner. Therefore, a seal member 32 such as an O-shaped ring is disposed in a contact site between an outer peripheral surface of the partition wall 21 and an inner surface at the proximal end of the insertion section 2.

In the partition wall 21, a through hole 21a configured to allow insertion of the bending wire 18 as the longitudinal member and a through hole 21b configured to allow insertion of the electrical signal line and the light guide cable 19 as the longitudinal members are formed. In this case, the bending wire 18 is arranged to be able to advance and retreat in a direction of the insertion axis of the insertion section 2 (the direction of the long axis; the direction indicated by the arrow Ax in FIG. 2) while being inserted into the through hole 21a. In this case, the through hole 21a in the partition wall 21 is configured to be able to maintain watertightness between the first space S1 and the second space S2. That is, a seal member 33 such as an O-shaped ring configured to ensure watertightness between the through hole 21a and the bending wire 18 while permitting advance and retreat in the direction of the insertion axis (the Ax direction) of the bending wire 18 is provided in the through hole 21a.

The electrical signal line or the light guide cable 19 extends from the distal end portion 11 in the insertion section 2, is inserted into the insertion section 2, then penetrates the through hole 21b, and is introduced into the operation section 3, as described above. The electrical signal line or the light guide cable 19 is the longitudinal member that further extends toward the universal cable 4, is inserted into the internal space of the universal cable 4, and is provided to extend to a distal end of the light guide connector 15 (see FIG. 1). Therefore, in the through hole 21b in the partition wall 21, the seal member 33 such as the O-shaped ring configured to ensure and maintain watertightness between the first space S1 and the second space S2 is also provided. Note that the electrical signal line or the light guide cable 19 does not positively move but has a margin slight enough to be movable in an axial direction in conjunction with a behavior exhibited when the insertion section 2 or the universal cable 4 is bent. Therefore, the seal member 33 is configured to be able to maintain watertightness while permitting the electrical signal line or the light guide cable 19 to slightly move in the axial direction.

Furthermore, the partition wall 21 is provided with a first check valve 22 configured to control circulation of gas inside the endoscope 1 (a detailed configuration will be described below; see FIG. 3, for example). The first check valve 22 is a valve member having a function of being able to circulate gas from the first space S1 to the second space S2 while blocking circulation of gas from the second space S2 to the first space S1.

Note that other constituent members disposed in the housing 3a in the operation section 3 are portions not directly related to the present invention, and hence illustration is omitted while detailed description of the constituent members is omitted.

The universal cable 4 is a cable member having an elongated tubular shape extending from the housing 3a in the operation section 3. The electrical signal line and the light guide cable 19, for example, among the above-described longitudinal members are inserted into and arranged in the universal cable 4, as described above. The light guide connector 15 is connected, as illustrated in FIG. 1, to a distal end of the universal cable 4. The light guide connector 15 is a connection member formed to be detachably attached to a socket portion provided in a light source apparatus not illustrated.

In the light guide connector 15, an air vent port 16 configured to cause the respective internal spaces of the universal cable 4 and the operation section 3 in the endoscope 1 (the second space S2) and an outside of the endoscope 1 to communicate with each other is formed. In the endoscope 1 according to the present embodiment, a cap member (not illustrated) configured to be detachably attached to the air vent port 16 is provided. The cap member is a cover member configured to close the air vent port 16 when mounted on the air vent port 16 and open the air vent port 16 when removed from the air vent port 16. Note that as a configuration of the air vent port 16 and the cap member, a configuration substantially similar to a configuration applied in a conventional endoscope (see, e.g., Japanese Patent Application Laid-Open Publication No. 2000-126111, described above), for example, is adopted. Therefore, detailed illustration and description of the configuration are omitted.

A detailed configuration of the first check valve 22 will be described below. The first check valve 22 mainly includes a cylinder 23, a piston 24, and a compression spring 25, for example, as illustrated in FIGS. 3 and 4.

The cylinder 23 is formed in a hollow cylindrical shape including openings 22a and 22b at both ends. Both the openings 22a and 22b connect to each other via an internal space of the cylinder 23. Therefore, the internal space of the cylinder 23 is penetrated. A proximal end side of the cylinder 23 is fixedly provided in a watertight manner for a hole portion 21c in the partition wall 21. Therefore, a seal member 36 such as the O-shaped ring is provided on an outer peripheral surface of the cylinder 23. Therefore, the cylinder 23 is configured such that when the cylinder 23 is fitted in the hole portion 21c in the partition wall 21, a seal member 36 is interposed between the outer peripheral surface of the cylinder 23 and an inner peripheral surface of the hole portion 21c in the partition wall 21 so that watertightness between the cylinder 23 and the hole portion 21c is ensured.

The piston 24 is a valve member provided movably in an axial direction of the cylinder 23 in a through space of the cylinder 23 and configured to open and close the opening 22a on a side facing the first space S1. The piston 24 receives an urging force of the compression spring 25 to always maintain a state illustrated in FIG. 3, i.e., a closed state of the opening 22a.

The compression spring 25 is an urging member including a coil spring, for example, configured to urge the piston 24 in one direction in the internal space of the cylinder 23. The compression spring 25 is disposed between the piston 24 and the opening 22b on a side facing the second space S2, for example. The compression spring 25 always urges the piston 24 in a direction indicated by an arrow X illustrated in FIG. 3.

In this case, a restriction section 23a configured to restrict movement of the piston 24 with the urging force of the compression spring 25 and a spring fixing section 23b configured to fix one end of the compression spring 25 are provided in the internal space of the cylinder 23. When the piston 24 is urged with the urging force of the compression spring 25 to move in the direction indicated by the arrow X within the cylinder 23, and a distal end of the piston 24 abuts on the restriction section 23a, the movement in the X direction of the piston 24 is restricted. The piston 24 closes the opening 22a in a watertight manner when brought into the state. Therefore, a seal member 26 such as the O-shaped ring is provided between the restriction section 23a and the piston 24.

Note that when air pressure AP1 in the first space S1 and air pressure AP2 in the second space S2 are substantially equal to each other (AP1≈AP2) in the internal space of the endoscope 1, the piston 24 is urged in the direction indicated by the arrow X with the urging force of the compression spring 25. When the air pressure AP2 in the second space S2 is higher than the air pressure AP1 in the first space S1 (AP1<AP2), the piston 24 is urged in the same direction as the direction indicated by the arrow X of the urging with the urging force of the compression spring 25. A state at the time is the state illustrated in FIG. 3. The first check valve 22 is configured such that circulation of gas between the first space S1 and the second space S2 is blocked when in the closed state illustrated in FIG. 3 (see symbol Air1 in FIG. 3).

On the other hand, when the air pressure AP1 in the first space S1 becomes higher than the air pressure AP2 in the second space S2 (AP1>AP2), the urging force of the compression spring 25 is set such that the piston 24 can move in an opposite direction to the direction indicated by the arrow X against the urging force of the compression spring 25. A state at that time is the state illustrated in FIG. 4. The first check valve 22 is configured such that gas in the first space S1 flows into the second space S2 via the cylinder 23 when the first check valve 22 enters the open state illustrated in FIG. 4 (see symbol Air2 in FIG. 4).

If the endoscope 1 according to the present embodiment thus configured is subjected to autoclave sterilization treatment, the endoscope 1 is first introduced into a sterilization chamber. At this time, the air vent port 16 in the light guide connector 15 in the endoscope 1 is brought into an open state (by removing a cap member, for example). In the state, the respective internal spaces of the universal cable 4 and the operation section 3 in the endoscope 1, i.e., the second space S2 and an external space of the endoscope 1 communicate with each other via the air vent port 16. Accordingly, the air pressure in the second space S2 and air pressure in the external space are substantially the same.

At this time, in the internal space of the endoscope 1, it is considered that the air pressure (AP1) in the first space S1 and the air pressure (AP2) in the second space S2 remain substantially equal to each other (AP1≈AP2). Therefore, in the state, the piston 24 is urged in the direction indicated by the arrow X with the urging force of the compression spring 25. Therefore, the closed state illustrated in FIG. 3 is maintained.

In the state, after the sterilization chamber is closed, autoclave sterilization treatment is started. FIG. 5 is a diagram illustrating, in the endoscope 1 according to the present embodiment, respective air pressure changes in the internal space (the first space and the second space) of the endoscope 1 at the time of autoclave sterilization treatment.

First, in a sterilization preparation process (see a time period Ta in FIG. 5), a setting is made such that pressurization and depressurization of an inside of the sterilization chamber (e.g., the external space of the endoscope 1) are repeatedly performed to eliminate air within the sterilization chamber, and the inside of the sterilization chamber is then pressurized to predetermined air pressure (a high-pressure state compared to atmospheric pressure). At this time, the second space S2 in the internal space of the endoscope 1 communicates with the inside of the sterilization chamber via the air vent port 16. Accordingly, the second space S2 is also pressurized to similar air pressure to air pressure within the sterilization chamber. If the air pressure within the sterilization chamber reaches the predetermined air pressure, a sterilization process is started with the state maintained (see a time period Tb in FIG. 5).

In the sterilization process, the air pressure (AP2) in the second space S2 becomes higher than the air pressure (AP1) in the first space S1. When the state is continued, vapor in the second space S2 slightly enters the first space S1 so that the air pressure (AP1) in the first space S1 gradually rises. However, the first space S1 and the second space S2 are separated by the partition wall 21, and the first check valve 22 is maintained in the closed state illustrated in FIG. 3. Therefore, the first check valve 22 blocks circulation of gas from the second space S2 to the first space S1 at this time (see the symbol Air1 in FIG. 3). As a result, a rise of the air pressure AP1 in the first space S1 is restricted (see a dotted line in FIG. 5).

When the sterilization process (the time period Tb) ends after a predetermined time period elapses, the air pressure within the sterilization chamber is reduced, and a drying process is started (see a time period Tc in FIG. 5). At this time, as the air pressure within the sterilization chamber is reduced, the air pressure (AP2) in the second space S2 of the endoscope 1 is also reduced. As a result, the air pressure (AP2) in the second space S2 becomes lower than the air pressure (AP1) in the first space S1. As a result, the piston 24 in the first check valve 22 moves in the opposite direction to the arrow X against the urging force of the compression spring 25 (the open state illustrated in FIG. 4). As a result, gas in the first space S1 flows into the second space S2 via the cylinder 23 (see symbol Air2 in FIG. 4). Thus, the air pressure (AP1) in the first space S1 also rapidly decreases (see a time period Tc in FIG. 5).

As described above, according to the above-described first embodiment, the partition wall 21 configured to separate the first space S1 and the second space S2 is provided in the internal space of the endoscope 1 and the partition wall 21 is further provided with the first check valve 22. The endoscope 1 is configured such that the external space of the endoscope 1 (the space within the sterilization chamber) and the second space S2 can communicate with each other by the air vent port 16 when autoclave sterilization treatment is performed. The first check valve 22 can block circulation of gas between the first space S1 and the second space S2 to prevent vapor from entering the first space S1 while restricting a rise in the air pressure in the first space S1 at the time of the sterilization process. In the drying process, the first check valve 22 is opened so that a small amount of vapor, which has entered the first space S1, can be made to flow into the second space S2 via the cylinder 23.

The bending operation mechanism 17, which tends to be a relatively large-sized constituent unit, is disposed on a side of a space outside the first space S1 where watertightness is to be ensured, i.e., on the second space S2 side. The configuration enables the first space S1 to be miniaturized. That is, a constituent portion configured to hold watertightness can be made small in size and light in weight.

Second Embodiment

Figure 6:
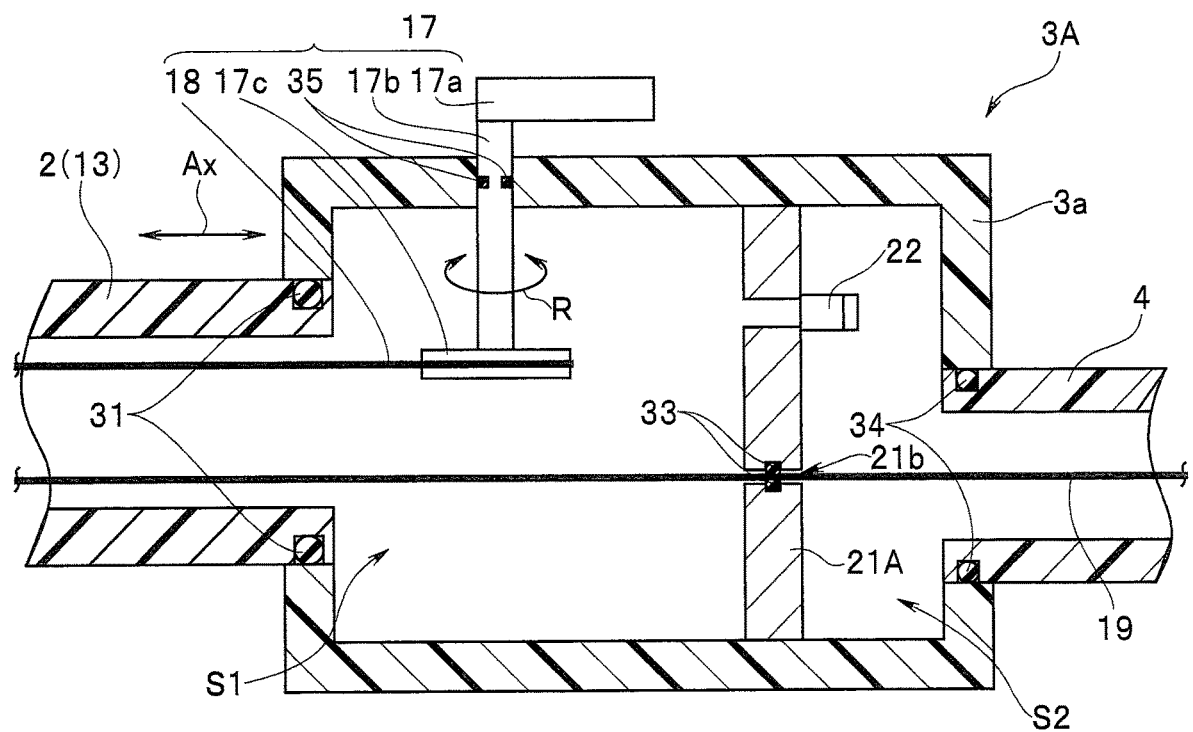
FIG. 6 is a diagram illustrating an outline of an internal configuration of a connection site among an insertion section, an operation section, and a universal cable in an endoscope according to a second embodiment of the present invention.

An endoscope according to a second embodiment of the present invention will be described below. FIG. 6 is a diagram illustrating an outline of an internal configuration of a connection site among an insertion section, an operation section, and a universal cable in the endoscope according to the second embodiment of the present invention. FIG. 6 is a diagram corresponding to FIG. 2 in the above-described first embodiment.

The endoscope according to the present embodiment basically has a configuration substantially similar to the configuration of the endoscope described in the above-described first embodiment. The endoscope according to the present embodiment slightly differs from the endoscope according to the first embodiment in a disposition site of a partition wall 21A as a wall member configured to separate a first space S1 and a second space S2 within an internal space of the endoscope, and accordingly only slightly differs from the endoscope according to the first embodiment in the configuration. Therefore, the same components as the components in the first embodiment are assigned the same reference numeral, and detailed description of the components is omitted.

In the endoscope according to the present embodiment, the partition wall 21A as the wall member configured to separate the first space S1 and the second space S2 within the internal space of the endoscope is provided inside an operation section 3A.

In the present embodiment, the first space S1 in the internal space of the endoscope 1 is a space including an internal space of an insertion section 2 out of spaces separated by the partition wall 21A. That is, the first space S1 in the present embodiment is a space including the internal space of the insertion section 2 and an internal space, closer to the insertion section 2, out of internal spaces of a housing 3a in the operation section 3A separated by the partition wall 21A.

In the present embodiment, the second space S2 means the space other than the first space S1 out of the two spaces separated by the partition wall 21A in the internal space of the endoscope 1. That is, the second space S2 is a space including the other internal space in the housing 3a in the operation section 3 and an internal space of a universal cable 4 (and a light guide connector 15) consecutively provided from the other internal space.

The partition wall 21A is formed using a substantially similar material to the material in the above-described first embodiment. The partition wall 21A is disposed to partition the internal space of the housing 3a in the operation section 3 into two regions. The partition wall 21A and the housing 3a are fixed to each other in a watertight manner. The second embodiment is similar to the first embodiment in that a through hole 21b configured to allow insertion of an electrical signal line and a light guide cable 19 is formed in the partition wall 21A.

Note that a through hole 21a configured to allow insertion of a bending wire 18 is not disposed in the partition wall 21A. This is because in the present embodiment, a bending operation mechanism 17 including the bending wire 18 is disposed inside the first space S1.

In the present embodiment, the partition wall 21A is also provided with a first check valve 22 configured to control circulation of gas inside the endoscope 1. A configuration of the first check valve 22 itself is entirely the same as the configuration described in the above-described first embodiment. Therefore, the first check valve 22 is a valve member having a function of enabling circulation of gas from the first space S1 to the second space S2 while blocking circulation of gas from the second space S2 to the first space S1. Other components are similar to the components in the first embodiment.

According to the above-described second embodiment thus configured, a similar effect to the effect in the above-described first embodiment can be obtained. In addition, according to the present embodiment, the bending operation mechanism 17 is also configured to be disposed within the first space S1 where watertightness is to be ensured. When thus configured, the bending operation mechanism 17 is also not exposed to vapor at the time of autoclave sterilization treatment in the present embodiment. Therefore, the bending operation mechanism 17 can be prevented from deteriorating.

When watertightness among the first space S1, the second space S2, and an external space is maintained, sealing of a sliding portion of a sliding member (e.g., a bending wire) can be eliminated, and sealing by a seal member 35 may be only performed in a rotation operation portion of a rotating shaft 17b in the operation lever 17a (an operation member). Therefore, the configuration enables stable watertightness inside the endoscope to be ensured.

Third Embodiment

Figure 7:
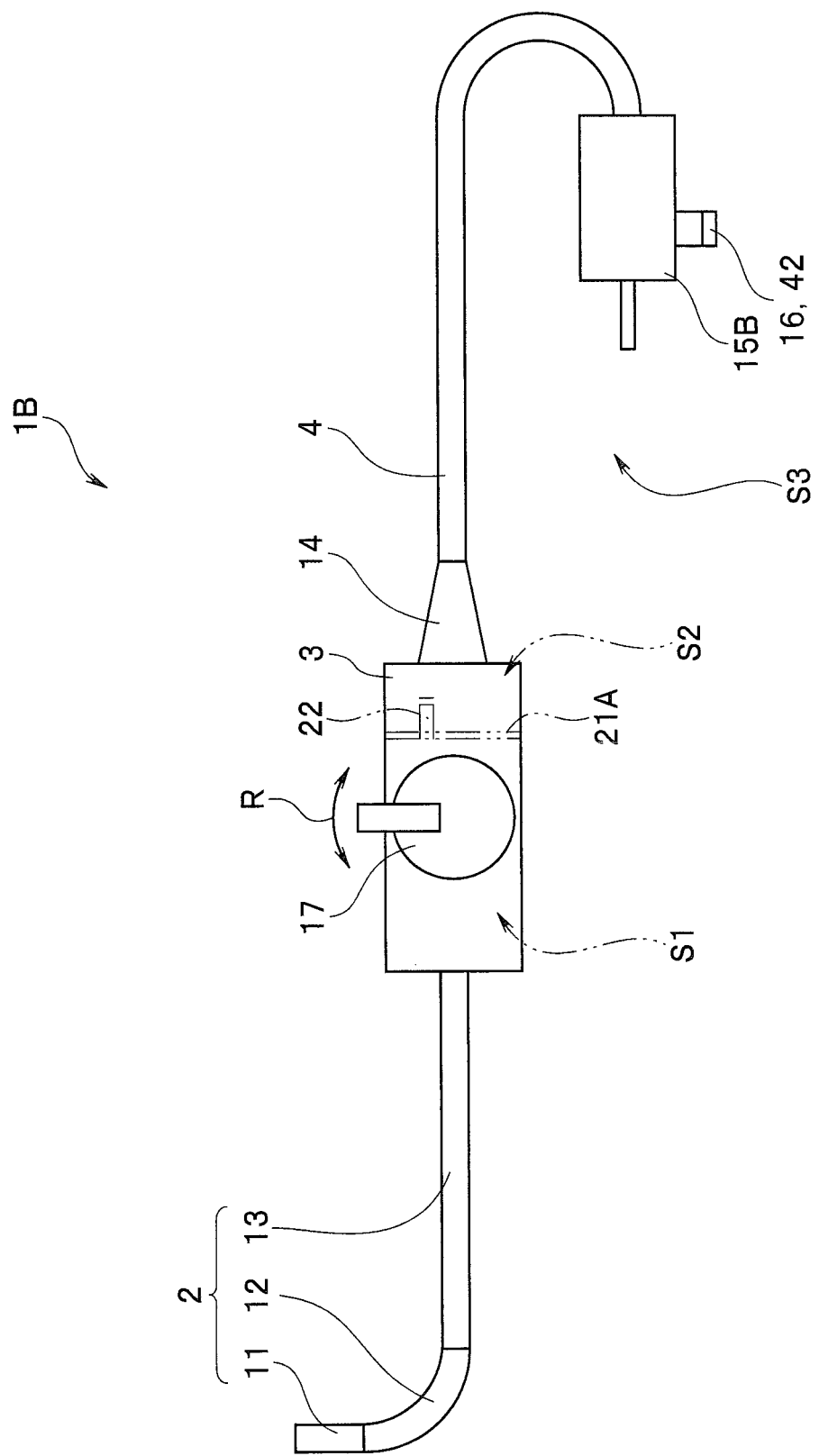
FIG. 7 is a diagram illustrating a schematic configuration of an endoscope according to a third embodiment of the present invention.
Figure 8:
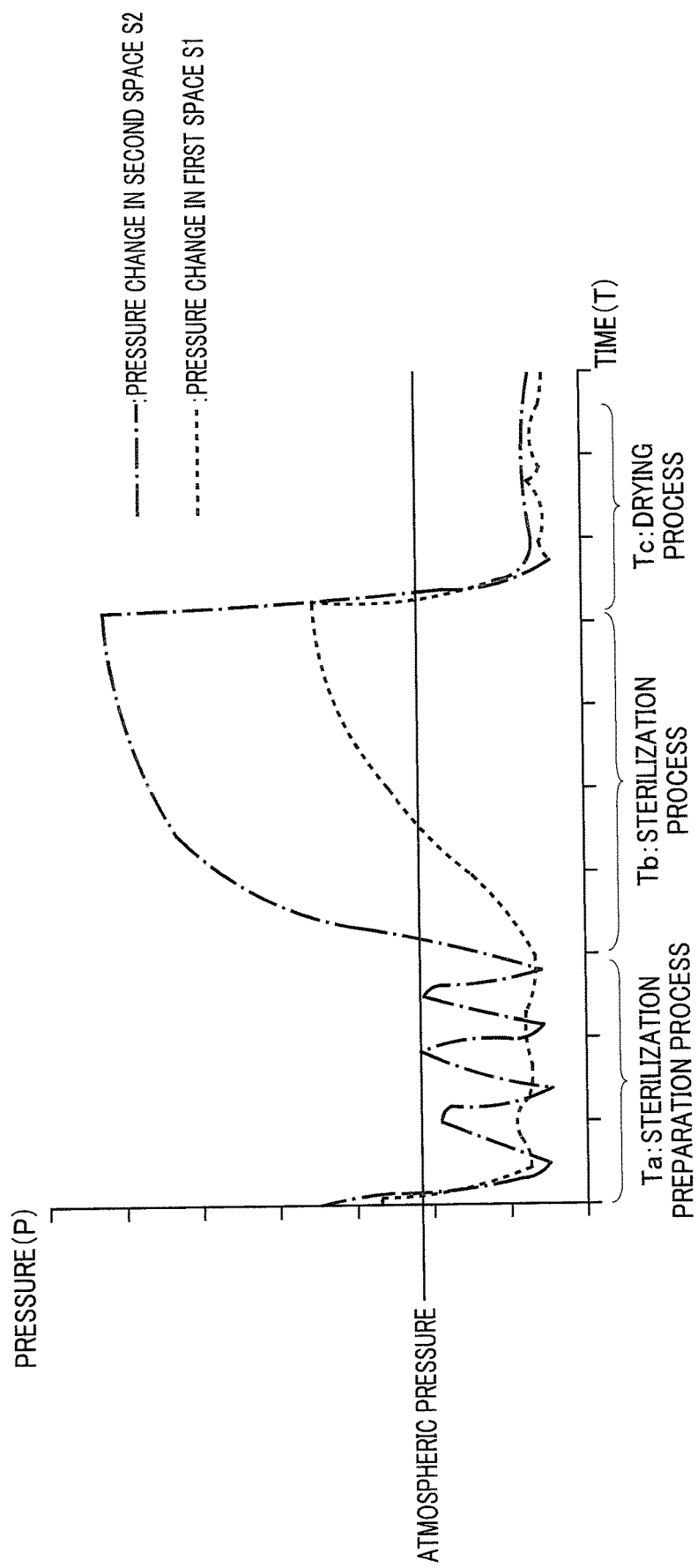
FIG. 8 is a diagram illustrating respective air pressure changes in an internal space (a first space and a second space) of the endoscope illustrated in FIG. 7 at the time of autoclave sterilization treatment.

An endoscope according to a third embodiment of the present invention will be described below. FIG. 7 is a diagram illustrating a schematic configuration of the endoscope according to the third embodiment of the present invention. FIG. 7 is a diagram corresponding to FIG. 1 in the above-described first embodiment. FIG. 8 is a diagram illustrating respective air pressure changes in an internal space (a first space and a second space) of the endoscope at the time of autoclave sterilization treatment in the endoscope according to the present embodiment.

An endoscope 1B according to the present embodiment basically has a configuration substantially similar to the respective configurations of the endoscopes described in the above-described first and second embodiments. The endoscope 1B according to the present embodiment differs from the endoscopes according to the first and second embodiments in that a second check valve 42 is further added to an air vent port 16 in a connector 15B.

A configuration of the second check valve 42 itself is similar to a configuration applied to a connector section in the conventional endoscope (see, e.g., Japanese Patent Application Laid-Open Publication No. 2000-157484; Patent Literature 2). More specifically, the configuration of the second check valve 42 is basically similar to the configuration of the first check valve 22 described in the above-described first embodiment.

To an arrangement of a partition wall and a check valve in the endoscope 1B according to the present embodiment, the configuration in the above-described first embodiment is also applicable as it is, or the configuration in the above-described second embodiment is also applicable as it is.

Note that an outline of an arrangement of a partition wall 21A is illustrated as a similar component to the component in the above-described second embodiment. Other components are the same as the components in the above-described first and second embodiments, and hence detailed description of the components are omitted.

In the endoscope 1B according to the present embodiment thus configured, a space closer to an insertion section 2 with respect to a partition wall 21A in an internal space of the endoscope 1B is set as a first space S1. A space closer to a universal cable 4 with respect to the partition wall 21A is set as a second space S2. An external space of the endoscope 1B, i.e., a space corresponding to a sterilization chamber when autoclave sterilization treatment is performed is indicated by a reference symbol S3.

In this case, when air pressure in the first space S1 is set as AP1 and air pressure in the second space S2 is set as AP2, a first check valve 22 enters an open state when AP1>AP2 is satisfied. When the air pressure in the second space S2 is set as AP2 and air pressure in the external space S3 is set as AP3, a second check valve 42 enters an open state when AP2>AP3 is satisfied.

When a pressure difference (AP1−AP2) occurring when the first check valve 22 enters the open state is set equal to PA, and a pressure difference (AP2−AP3) occurring when the second check valve 42 enters the open state is set equal to PB, both the check valves 22 and 42 are preferably set to respectively enter the open states when PA<PB is satisfied.

According to the above-described third embodiment thus configured, a similar effect to the respective effects in the above-described first and second embodiments can be obtained. In addition, according to the present embodiment, the second check valve 42 configured to control circulation of gas between the internal space (the second space S2) and the external space S3 of the endoscope is provided in addition to the first check valve 22 configured to control circulation of gas between the two spaces (the first space S1 and the second space S2) separated by the partition wall 21A in the internal space of the endoscope. Therefore, a rise in the air pressure in the first space S1 can be more restricted and a rise in the air pressure in the second space S2 can also be more restricted than the rise in the first embodiment, as illustrated in FIG. 8. In a drying process, the first check valve 22 is opened so that a slight amount of vapor, which has entered the first space S1, can be made to flow into the second space S2 via a cylinder 23.

Entrance of vapor into the internal space (the first space S1 and the second space S2) of the endoscope can be more reduced at the time of autoclave sterilization treatment. Accordingly, components inside the endoscope can be further prevented from deteriorating.

Fourth Embodiment

Figure 9:
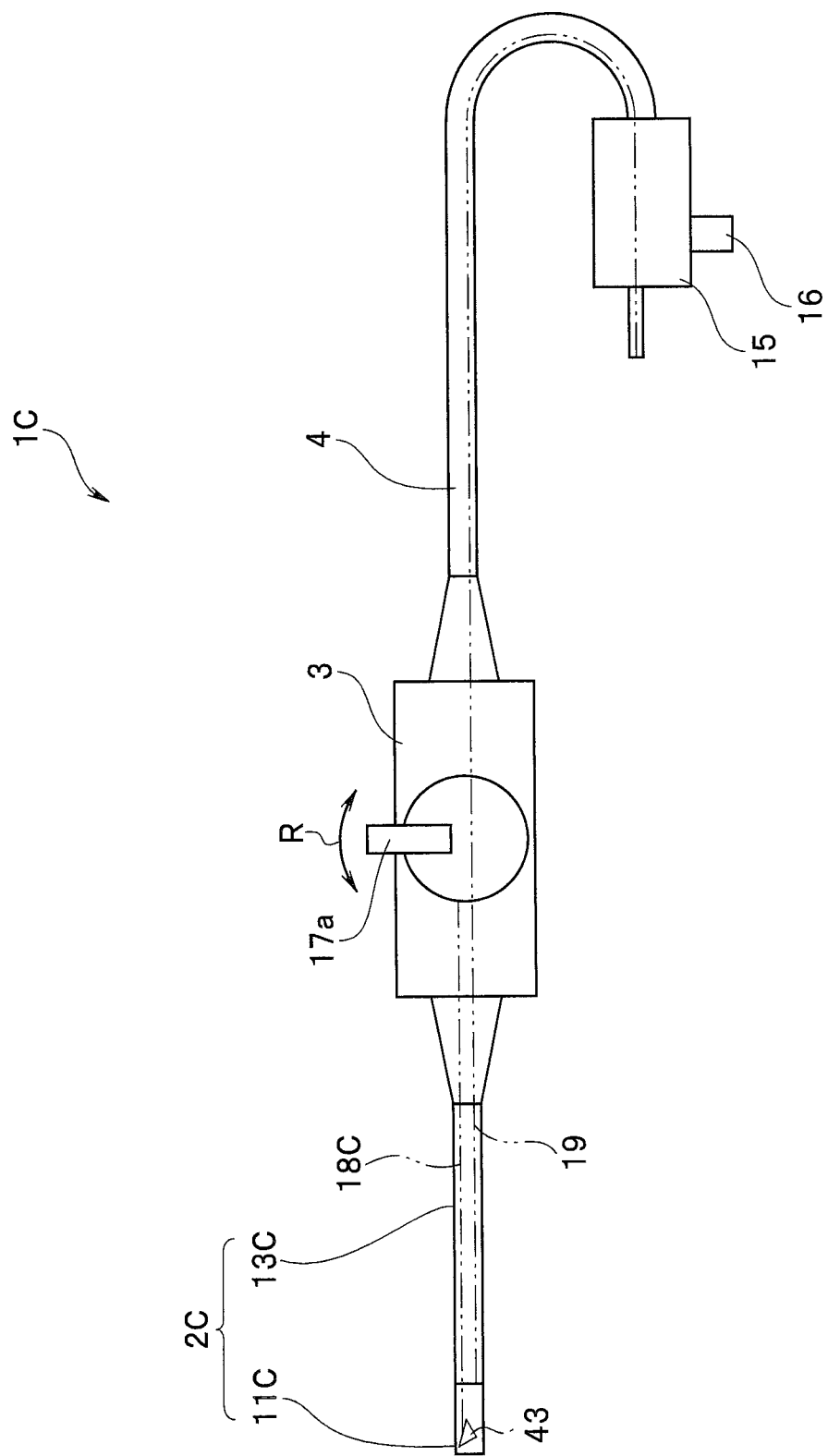
FIG. 9 is a diagram illustrating a schematic configuration of an endoscope according to a fourth embodiment of the present invention.

Then, an endoscope according to a fourth embodiment of the present invention will be described below. FIG. 9 is a diagram illustrating a schematic configuration of the endoscope according to the fourth embodiment of the present invention. FIG. 9 corresponds to FIG. 1 in the above-described first embodiment, and corresponds to FIG. 7 in the above-described third embodiment.

An endoscope 1C according to the present embodiment is a rigid endoscope composed of a rigid cylindrical member including no site having flexibility in an insertion section 2C. The endoscope 1C according to the present embodiment mainly includes the insertion section 2C, an operation section 3, and a universal cable 4, for example.

The insertion section 2C is a constituent section configured to be inserted into a body cavity of a subject when used as the endoscope 1C. The insertion section 2C does not have flexibility, and is formed in a rigid elongated tubular shape as a whole. The insertion section 2C is configured in a form in which a distal end portion 11C and a rigid tube 13C are consecutively provided in the order from a distal end side.

Longitudinal members, e.g., a prism traction wire 18C and a light guide cable 19 are inserted into and arranged in the insertion section 2C. The prism traction wire 18C constitutes a part of an operation mechanism configured to perform an operation for changing a direction of a prism 43 for visual field change provided inside the distal end portion 11C and switching an observation visual field. Therefore, the prism traction wire 18C is inserted into the insertion section 2C from the distal end portion 11C in the insertion section 2C, and is disposed up to a prism operation mechanism (not illustrated) inside the operation section 3. The prism traction wire 18C is configured to be able to advance and retreat in an axial direction of the insertion section 2C upon receiving an operation input from the prism operation mechanism (not illustrated). The light guide cable 19, for example, is inserted into the insertion section 2C and the operation section 3 from the distal end portion 11C in the insertion section 2C, and is further inserted into the universal cable 4.

To other components, similar components to the components described in each of the above-described embodiments are respectively applied. That is, in the endoscope 1C according to the present embodiment, to components such as an operation section, a universal cable, and a connector and components (a partition wall, a first check valve, a second check valve, etc.) inside each of the components, the components in the first embodiment can also be applied as they are, or the components in the second embodiment can also be applied as they are. Further, the components in the third embodiment can also be applied as they are.

Note that similar components to the components in the above-described first embodiment are applied in the present embodiment. Same components as the components in each of the above-described embodiments are applied to the other components, and hence detailed description of the components is omitted.

According to the above-described fourth embodiment thus configured, an entirely similar application can also be made to a rigid endoscope, and an entirely similar effect can be obtained.

Although members such as a bending wire, a signal line, a light guide cable, and a prism traction wire have been described as examples of a longitudinal member configured to allow insertion of an insertion section in the endoscope according to each of the above-described embodiments, a member configured to allow insertion of the insertion section can correspond to the above-described longitudinal member in addition to the members.

If the endoscope according to each of the above-described embodiments has a form in which a longitudinal member is not provided, a partition wall need not be provided with a through hole. Accordingly, the form can contribute to a further improvement of watertightness between a first space and a second space separated by the partition wall.

As a configuration for the form, longitudinal members such as a signal line can be eliminated using wireless transmission means for transmission of an image pickup signal, a control signal, or the like in a configuration in which an operation mechanism is arranged within a first space and a bending wire or the like is not inserted into a partition wall (the configuration in the above-described second embodiment), for example. In addition, if a configuration in which illumination means is further provided in a distal end portion in an insertion section is used, a light guide cable can be eliminated. By the configuration, a through hole can be eliminated from the partition wall.

The present invention is not limited to the above-described embodiments, and it is needless to say that various modifications and applications can be made without departing from the spirit of the invention. Further, the above-described embodiments include inventions in various stages, and various inventions can be extracted by appropriate combinations in a plurality of constituent elements disclosed. Even if some of all the constituent elements illustrated in the one embodiment are removed, a problem to be solved by the invention can be solved and an effect of the invention is obtained, a configuration from which the constituent elements are removed can be extracted as the invention. Further, components over the different embodiments may be appropriately combined. The present invention is not constrained by specific embodiments except as limited by the appended claims.

The present invention is also applicable to not only an endoscope control apparatus in a medical field but also an endoscope control apparatus in an industrial field.

What is claimed is:

1. An endoscope comprising:
   an insertion section configured to be inserted into a subject;
   an operation section provided on a proximal end side of the insertion section;
   a rigid partition wall provided inside the insertion section or inside the operation section, the partition wall being configured to maintain watertightness between a first internal space including an inside of the insertion section and a second internal space formed proximally relative to the first internal space; and
   a first check valve provided in the partition wall, the first check valve being configured to block circulation of gas from the second internal space to the first internal space and circulate gas from the first internal space to the second internal space.

2. The endoscope according to claim 1, further comprising a longitudinal member inserted into and arranged in the insertion section,
   wherein the longitudinal member is provided to extend in the operation section, and
   the partition wall includes a through hole configured to allow passage of the longitudinal member from the first internal space to the second internal space.

3. The endoscope according to claim 2, wherein the longitudinal member is a wire movable in a direction of a long axis of the insertion section.

4. The endoscope according to claim 2, wherein the longitudinal member is one of a signal line or a light guide cable.

5. The endoscope according to claim 1, further comprising
   a second check valve provided proximally relative to the operation section, the second check valve being configured to circulate gas from the second internal space to an external space and block circulation of gas from the external space to the second internal space.

6. The endoscope according to claim 5, further comprising
a universal cable extending proximally from the operation section, wherein
the universal cable has one end at which a connector is provided,
a longitudinal member is extended inside the universal cable, and
the second check valve is disposed in the connector.

7. The endoscope according to claim 6, wherein the longitudinal member is one of a signal line or a light guide cable.

8. The endoscope according to claim 5, wherein the second check valve is configured to:
circulate gas from the second internal space to the external space when air pressure in the second internal space becomes higher than air pressure in the external space, and
block circulation of gas from the external space to the second internal space when the air pressure in the second internal space and the air pressure in the external space become equal to each other or the air pressure in the external space becomes higher than the air pressure in the second internal space.

9. The endoscope according to claim 5, wherein
when a pressure difference occurring when the first check valve enters an open state is set equal to PA, and a pressure difference occurring when the second check valve enters an open state is set equal to PB,
both the first check valve and the second check valve are set to respectively enter the open states when PA<PB is satisfied.

10. The endoscope according to claim 1, wherein the first check valve is configured to:
circulate gas from the first internal space to the second internal space when air pressure in the first internal space becomes higher than air pressure in the second internal space, and
block circulation of gas from the second internal space to the first internal space when the air pressure in the first internal space and the air pressure in the second internal space become equal to each other or the air pressure in the second internal space becomes higher than the air pressure in the first internal space.

* * * * *